United States Patent

Groves et al.

[11] Patent Number: 6,002,026
[45] Date of Patent: Dec. 14, 1999

[54] CATALYTIC OXYGENATION OF HYDROCARBONS BY METALLOPORPHYRIN AND METALLOSALEN COMPLEXES

[75] Inventors: John T. Groves, Princeton, N.J.; Tommaso Carofiglio; Marcella Bonchio, both of Padua, Italy; Anthony Sauve, Princeton, N.J.

[73] Assignee: The Trustees of Princeton University, Princeton, N.J.

[21] Appl. No.: 08/760,849

[22] Filed: Dec. 5, 1996

Related U.S. Application Data

[63] Continuation of application No. 08/686,663, Jul. 26, 1996, abandoned.

[51] Int. Cl.$^6$ .......................... C07D 301/06; C07C 45/00; C07C 35/22; C07C 35/08
[52] U.S. Cl. .......................... 549/533; 568/360; 568/818; 568/836
[58] Field of Search .......................... 549/533; 568/360, 568/818, 836

[56] References Cited

U.S. PATENT DOCUMENTS

| | | | |
|---|---|---|---|
| 4,322,562 | 3/1982 | Tovrog et al. | 568/401 |
| 4,822,899 | 4/1989 | Groves et al. | 549/533 |
| 4,892,941 | 1/1990 | Dolphin et al. | 540/145 |
| 4,895,680 | 1/1990 | Ellis, Jr. et al. | 260/410.9 R |
| 4,895,682 | 1/1990 | Ellis, Jr. et al. | 260/410.9 R |
| 4,900,871 | 2/1990 | Ellis, Jr. et al. | 568/399 |
| 4,970,348 | 11/1990 | Ellis, Jr. et al. | 568/399 |
| 5,077,394 | 12/1991 | Dolphin et al. | 530/505 |
| 5,120,882 | 6/1992 | Ellis, Jr. et al. | 568/910 |
| 5,212,300 | 5/1993 | Ellis, Jr. et al. | 540/145 |
| 5,220,080 | 7/1993 | Lyons et al. | 568/910 |
| 5,280,115 | 1/1994 | Ellis, Jr. et al. | 540/145 |
| 5,347,057 | 9/1994 | Khan | 568/910 |
| 5,571,908 | 5/1996 | Wijesekera et al. | 540/145 |
| 5,608,054 | 3/1997 | Wijesekera e al. | 540/145 |

OTHER PUBLICATIONS

Sheldon, Roger A., et al. "Metal–Catalyzed Oxidations of Organic Compounds" Mechanistic Principles and Synthetic Methodology Including Biochemical Processes (1981), pp. 112, 113 and 119.

Ohtake, et al., "The Highly Efficient Oxidation of Olefins, Alcohols, Sulfides and Alkanes with Heteroaromatic N–Oxides Catalyzed by Ruthenium Porphyrins", pp. 867–887, Heterocycles, vol. 40, No. 2, 1995.

Mlodnicka, et al., "Oxidations Catalyzed by Ruthenium Porphyrins", Metalloporphyrins Catalyzed Oxidations, pp. 121, 130, and 131 1994.

James, Brian R., "The Use of Group VIII Metal Complexes for Catalytic Oxidation and Oxygen Transfer Reactions", Fundamental Research in Homogenous Catalysis, pp. 309–315 (1986).

Birnbaum, et al., "Electronic Structures of Halogenated Ruthenium Porphyrins", Inorg. Chem. 34, pp. 1751 and 1752 (1995).

(List continued on next page.)

*Primary Examiner*—John Kight
*Assistant Examiner*—Rita Desai
*Attorney, Agent, or Firm*—Hoffmann & Baron, LLP

[57] ABSTRACT

The present invention relates to novel oxidative processes for substrates such as olefins, alkanes, aromatics and alcohols using metallic porphyrin or salen catalytic complexes which have been specifically designed to maximize catalytic activity, thereby enhancing efficiency, selectively and speed of oxidation of these substrates. The choice of the substituents in the metallic complexes may be varied, but must be chosen to prevent specific ligand set arrangements known to be stable and therefore less catalytically efficient. Coordination complexes, particularly porphyrins and salens having nitrosyl axial ligands and electron-withdrawing peripheral substituents are preferred. Ruthenium coordination metals are the preferred metal center, with the highly reactive catalytic species found to be $Ru^{III}$.

10 Claims, 5 Drawing Sheets

OTHER PUBLICATIONS

Groves, et al., "Nitrous Oxide Activation by a Ruthenium Porphyrin", J. Am. Chem. Soc. 117, pp. 5594–5594 (1995).

Ohtake, et al., "Highly Efficient Oxidation of Alkanes and Alkyl Alcohols with Heteroaromatic N–Oxides Catalyzed by Ruthenium Porphyrins", J. Am. Chem Soc. 114, pp. 10660–10662. (1992).

Aoyama et al, Catalytic Reaction s of Metalloporphyrins.,J. Org. Chem. 1987,52, 2555–2559.

Wing–Kin Cheng et al, Osmium–(V),–(IV) and –(III) complexes with Tetradentate Dianionic Chelating Ligands, J. Chem. Soc. Dalton Trans. 1992 pp. 91 to 96.

Takagi, S. et al, Inorg. Chim. Acta, 1990, 173(2), pp. 215–221, online data.

Murahasi, S.I. et al, Tetrahedron Letters, 1995, 36(44), pp. 8059–8062.

Khan, M.M. e tal, J. Mol. Catal. 1992, 72(3), pp. 271–282.

Muccigrosso, D.A. et al, Inorg. Chem. 1983, 22(6), pp. 960–965.

Ercolani, C. et al, J. Chem. Soc., Dalton Trans., 1991, 5, pp. 1317–1321.

CATALYTIC OXYGENATION OF HYDROCARBONS BY METALLOPORPHYRIN AND METALLOSALEN COMPLEXES

This is a continuation of U.S. application Ser. No. 08/686,663, filed on Jul. 26, 1996, now abandoned.

FIELD OF THE INVENTION

The present invention relates to catalytic oxidation of hydrocarbons using metallic porphyrin or salen complexes. The metallic porphyrin or salen complexes of the present invention are designed to efficiently produce high yields of oxygenated products selectively and rapidly under conditions conducive to commercial production and scale-up. More particularly, the present invention relates to novel oxidation processes and in some cases novel oxidation compounds which can be used to oxidize olefins to their corresponding epoxides, alkanes to alcohols and subsequently to their corresponding ketones, as well as the hydroxylation of aromatics to phenols and their corresponding quinones.

BACKGROUND OF THE INVENTION

The efficient oxygenation of the hydrocarbons has enormous commercial value for the production of commodity chemicals and for many important products made therefrom. For example, nylon is one such product which has enormous commercial applications and which is made from starting materials, i.e. cyclohexane, which must first be oxidized into alcohol and ketone intermediate compounds during the manufacture of nylon. The oxygenation of cyclohexane, however, is extremely expensive and inefficient, having a conversion of only 3–4%. Sufficient oxygenation of various saturated hydrocarbons has long been a difficult challenge which has provoked the search for efficient and cost effective oxidation catalysts and processes for use in the chemical industry.

Toward this end, transition metal catalysts have been studied for some time for their use as oxidation catalysts for saturated hydrocarbons. More recently, the use of metallic porphyrin complexes have been reported as effective oxidation catalysts using certain substrates, oxidants and process parameters. For example, U.S. Pat. No. 4,822,899 to Groves et al., describes the use of metallic porphyrin complexes as catalysts in epoxidation reactions. The process disclosed in this reference involves adding to a solution of metallic porphyrin catalyst an olefin or mixture of olefins to form a reaction solution. The reaction solution is purged with an oxidizing agent, e.g. commercially pure oxygen or air, and the reaction is conducted at ambient conditions for 24 hours. The results after 24 hours shows a maximum turnover rate of 45.4, as shown in Example 8, in the Table, Column 5. The turnover rate is the number of molecules of oxidized product turned out per each molecule of catalyst for a given time period. Thus, while U.S. Pat. No. 4,822,899 demonstrated the ability to use metallic porphyrin complexes as oxidation catalysts using air as the oxidant and under ambient conditions, the efficiency of such reactions even under the best of reaction conditions, e.g. under optimum temperature and pressure parameters, is comparatively low. That is, the turnover rate and yields represented an improvement over previous efforts but did not approach the level useful for commercial scale-up.

Subsequent efforts using metallic porphyrins as oxidation catalysts for olefins, alcohols, sulfides and alkanes using heteroaromatic N-oxides, demonstrated that the addition of strong mineral acids such as HCl and HBr enhances oxidation selectively and efficiently. See Ohtake et al. Heterocyles, Vol. 40, No. 2, pp. 867–887 (1995); Ohtake et al., J. Am. Chem. Soc., 114, 10660–10662 (1992). These references suggest that halogens coordinate as an axial ligand and accelerate the deoxygenation of N-oxide by ruthenium porphyrin. The use of such acids, however, may decompose some of the end products and result in halogen by-products which require appropriate separation and handling. Moreover, certain aromatics, such as benzene, were reported by Ohtake et al. as not being useful oxidative substrates. Additionally, the highest turnover rate described in Ohtake et al. over a period of 24 hours with the addition of these mineral acids was shown as 12,500. See J. Am. Chem. Soc., 114, 10661 (1992).

The use of a nitro group on a coordinated ligand has been reported in the literature. See Sheldon R. A.; Kochi J. K., Metal-Catalyzed Oxidation of Organic Compounds, p. 112–113, Academic Press (1981). The nitro group, however, is used to transfer oxygen to a substrate, i.e. to oxidize the substrate. This reference shows that the oxidation state of the metal does not change. This is in sharp contrast to the present invention where the nitrosyl group present in the porphyrin or salen ligand structure remains intact and the oxidation state of the metal center changes to the highly active $M^{III}$ species.

U.S. Pat. No. 4,900,871 to Ellis, Jr. et al., discloses iron coordination complexes containing a halogenated ligand. The iron porphyrin complex is disclosed as having $Fe^{II}$ and $Fe^{III}$ states and the improvement in oxidation of alkanes by contact with air or oxygen is reported as being due to the introduction of halogen into the coordination complex. Oxidation of propane using such complexes show a maximum turnover of 583.1 per 1.5 hours at 150° C. and a maximum turnover of 849 per 6 hours at 80° C. using isobutane as the substrate. This patent states in column 7, line 29, that halogenating the ligand of the iron coordination complex improves activity but has little or no effect on activity where the metal is other typical transition metals such as manganese or chromium. Furthermore, these porphyrins have been reported as being free radical initiators rather than catalysts per se. See Grinstoff, M. W.; Hill, M. G.; Labinger, J. A.; Gray H. B., Science, 1994, 264, 1311–1313.

U.S. Pat. No. 5,280,115 to Ellis, Jr. et al. discloses metal complexes of porphyrin catalysts for the oxidation of alkanes where the metal may be ruthenium. The porphyrin ring has nitro groups attached thereto in the meso and/or β-pyrrolic positions.

U.S. Pat. No. 4,895,680 to Ellis, Jr. et al. discloses nitride-activated metal coordination complexes such as M-X where M is a transition metal and X is a nitride on the oxidation of alkanes. The turnovers/hour (T.O./hr.) using nitride-activated Fe, Cr and Mn porphyrins are relatively low. For example, oxidation of cyclohexane to cyclohexanol and cyclohexanone using the nitride-activated catalysts showed T.O./hr. values of 33 and 23 and 27 for Cr(TPP)N, Mn(TPP)N and [Fe (TPP)]$_2$N respectively.

Also present in the literature is a report on the theoretical existence of a ruthenium IV ($Ru^{IV}$) porphyrin radical species derived from a $Ru^{III}$ precursor. See Mlodnicka, T., James, B. R., Metalloporphyrin Catalyzed Oxidations, 121–148, Klewer Academic Publishers, (1994). This reference used a phosphine ligand and iodosylbenzene as an oxidant to achieve low oxidation product yields and low turnovers on hydrocarbon substrates such as cyclohexane, styrene, norbornene and stilbene (see Table 1, p. 131). The experiments reported therein showed turnovers of 1.3–130/6 hrs. It should be mentioned that such low catalytic results occurred notwithstanding the use of norbornene, a relatively reactive substrate, a halogenated porphyrin and in the presence of an exotic non-commercial oxidant iodosylbenzene.

The present invention represents a significant improvement over the prior art oxidation processes which employ metallic porphyrin complexes as oxidative catalysts. The efficiency, selectivity and speed have been significantly improved over the prior art without the use of mineral acids, and such difficult substrates as cyclohexanes and benzene have been oxygenated efficiently using the present invention. Thus, the present invention addresses the long sought need of finding a means to rapidly and efficiently oxidize commercially important substrates such as olefins, alkanes, aromatics, and alcohols (aliphatic or aromatic) by carefully designing the porphyrin or salen complex and the associated ligands. The coordination complexes of the present invention are designed by selecting substituents, both on the external structure and the internal ligand set, such that the maximum activity of the catalytic metal can be obtained. The choice of substituents is dictated by the need to control the electronic structure of the catalyst to prevent or minimize the formation of a stabilized ligand set adjacent the metal, as well as to minimize or prevent the formation of stabilized electron configurations on the metal per se a phenomenon known as disproportination.

SUMMARY OF THE INVENTION

The present invention relates to novel oxidative processes for substrates such as olefins, alkanes, aromatics and alcohols using metallic porphyrin or salen catalytic complexes which have been specifically designed to maximize catalytic activity, thereby enhancing efficiency, selectively and speed of oxidation of these substrates. The choice of the substituents in the metallic complexes may be varied, but must be chosen to prevent specific ligand set arrangements known to be stable and therefore less catalytically efficient.

The present invention has discovered that when the metal catalyst is in the $M^{III}$-P state, or its equivalent, and the peripheral substituents on the porphyrin or salen macrocycle structure are electron-withdrawing groups, the activity of the catalyst is remarkably and synergistically improved over prior art catalysts. M represents the coordination metal and P represents the coordination ligand attached thereto. This $M^{III}$-P species can be achieved using several pathways further described herein. The highly active catalysts of the present invention can be formed prior to catalysis or they can be formed in situ during the catalysis steps of oxidizing hydrocarbons.

Thus, in one embodiment, the present invention relates to a method of catalyzing the oxidation of hydrocarbons including contacting in the presence of an oxidant under reaction conditions said hydrocarbon with a metallo macrocyclic catalyst complex selected from the group consisting of porphyrins, salens and mixtures thereof, said catalyst complex having electron withdrawing substituents on its periphery and a highly reactive $M^{III}$ species or its equivalent contained within which catalytically effectuates rapid formation of oxidized hydrocarbon product.

In another embodiment of the present invention, a coordination ligand/transition metal complex having a nitrosyl axial liquid on the metal is described. The coordination ligand is preferably a porphyrin or salen structure which may optionally have various substitutions on its periphery. Preferably the transition metal is ruthenium and the peripheral substitutions on the coordination ligand are electron-withdrawing groups. These complexes represent novel catalysts for the oxidation of hydrocarbons.

In another embodiment, the present invention relates to a method of catalyzing the oxidation of hydrocarbons using high activity porphyrin metal complexes which includes the steps of (i) providing a coordination ligand "P" having electron-withdrawing substituent groups on its periphery and containing within it a low activity metallic species selected from the group consisting of dioxo—$M^{VI}$, XY—$M^{IV}$ and Z—$M^{II}$; (ii) reducing or oxidizing said low activity metallic species with a suitable reducing agent to obtain an $M^{III}$ species or its equivalent; (iii) contacting said $M^{III}$ species or its equivalent with said hydrocarbon in the presence of an oxidant to effectuate said catalysis of said hydrocarbon, wherein M is Ru, Os, Rh, Ir, Nb, Re or Tc; X and Y may be the same or different and are oxygen or a halogen; and Z is CO or a weakly coordinating ligand such as an alcohol, ether or acetonitrile. Preferably the coordination ligand is a porphyrin or salen, but other ligands which coordinate with the metal center to form a complex and stabilize the complex in the desired oxidation state are contemplated.

In addition to the novel catalytic processes of the present invention, the present invention further includes novel metalloporphyrin complexes used in the process which generate $M^{III}$ centers and have electron-withdrawing substituents on the ligand peripheral structure. Such novel complexes particularly include those with halogen peripheral substituents on a porphyrin ligand having $Ru^{II}$ at its center. These complexes generate $Ru^{III}$ as the highly active species in the presence of oxidants.

The catalysts and catalytic processes of the present invention greatly enhance the efficiency, selectivity and yield of oxidized substrate products. The turnover rate, i.e. the number of molecules of oxidized products per molecule of catalyst as measured over a given time period is exponentially increased over those processes of the prior art, and in particular, the aforementioned processes reported by Ohtake et al. Turnover rates of 800 to 1000 per minute have been obtained. Such results are remarkable when compared to those obtained by the prior art processes which measured turnover rates of 12,500 per 24 hour periods.

The present invention includes oxidation of a wide variety of compound types, including olefins, alkanes, aromatics, alcohols and the like. For example, in one embodiment, the catalysts of the present invention are used to convert olefins to epoxides. In another embodiment, the catalysts are used to convert alkanes to alcohols and subsequently to their corresponding ketones. In a still further embodiment, the catalysts are used in the hydroxylation of aromatics to phenols and further oxidized to their corresponding quinones.

For purposes of this invention $M^{+3}$ and $M^{III}$ will be used interchangeably and will designate the same highly active species. Likewise, the use of equal Roman and Arabic numbers designating other chemical species will also be intended to refer to the same species.

DETAILED DESCRIPTION OF THE INVENTION

It has been discovered that metal porphyrins and salen complexes can be made to function as exceptionally fast or "hot" catalysts for the oxidation of hydrocarbons provided certain conditions and structures of the complexes are present. While these conditions and structures can be organized into at least two main categories, they all serve to function to control the electronic configuration of the catalyst complex and thereby promote the formation of a highly active metal ion species for efficient transfer of oxygen to a hydrocarbon substrate.

One category of catalysts and processes of the present invention concerns the use of metallic and salen porphyrin complexes having an axial nitrosyl coordinating ligand which remains present and intact throughout the catalysis reaction. The peripheral substituents on the porphyrin may be selected from a wide variety of moieties, depending on the substrate and oxidant chosen. As previously mentioned, the present invention seeks to prevent the hydrocarbon oxidation from occurring in the presence of metal oxidation states which are relatively stable and therefore relatively slow in their ability to catalyze oxygenation of hydrocarbons. For example, the formation of a dioxo-metal, as discussed in the aforementioned U.S. Pat. No. 4,822,899, is prevented in the present invention by the presence of the nitrosyl axial ligand, a very strong coordinating ligand which renders the metal center more positively (electrophilically) charged. Due to the strong electron withdrawing effect of the nitrosyl on the metal center, the metal becomes highly activated. As previously mentioned, the combination of the nitrosyl axial ligand which remains intact and electron withdrawing groups on the periphery of the coordination ligand are unique to the present invention. The present invention has discovered through experimentation that the nitrosyl imparts activity to the metal cation but does not itself get oxidized to —$NO_2$, as was reported by the aforementioned Sheldon and Kochi reference. The original oxygen on the nitrosyl is still present on the nitrogen at the end of catalysis and this has been confirmed in the present invention by the technique of oxygen isotopic labeling.

Another category of catalysts and processes of the present invention which also involves providing an electronic configuration to the metal coordination complex which favors a highly reactive metal center are those having (i) a macrocyclic coordination metal complex having a porphyrin or salen ligand or mixtures thereof and having electron withdrawing substituent groups on the periphery of said ligand and (ii) containing within the complex a highly reactive $M^{III}$ species such as $R^{III}$, or its equivalent. It has been determined that a coordination complex having the $M^{III}$ ion species or its equivalent, e.g. $R^{III}$ renders the catalyst exceptionally active in its ability to catalyze the oxidation of hydrocarbons.

Figure 1:
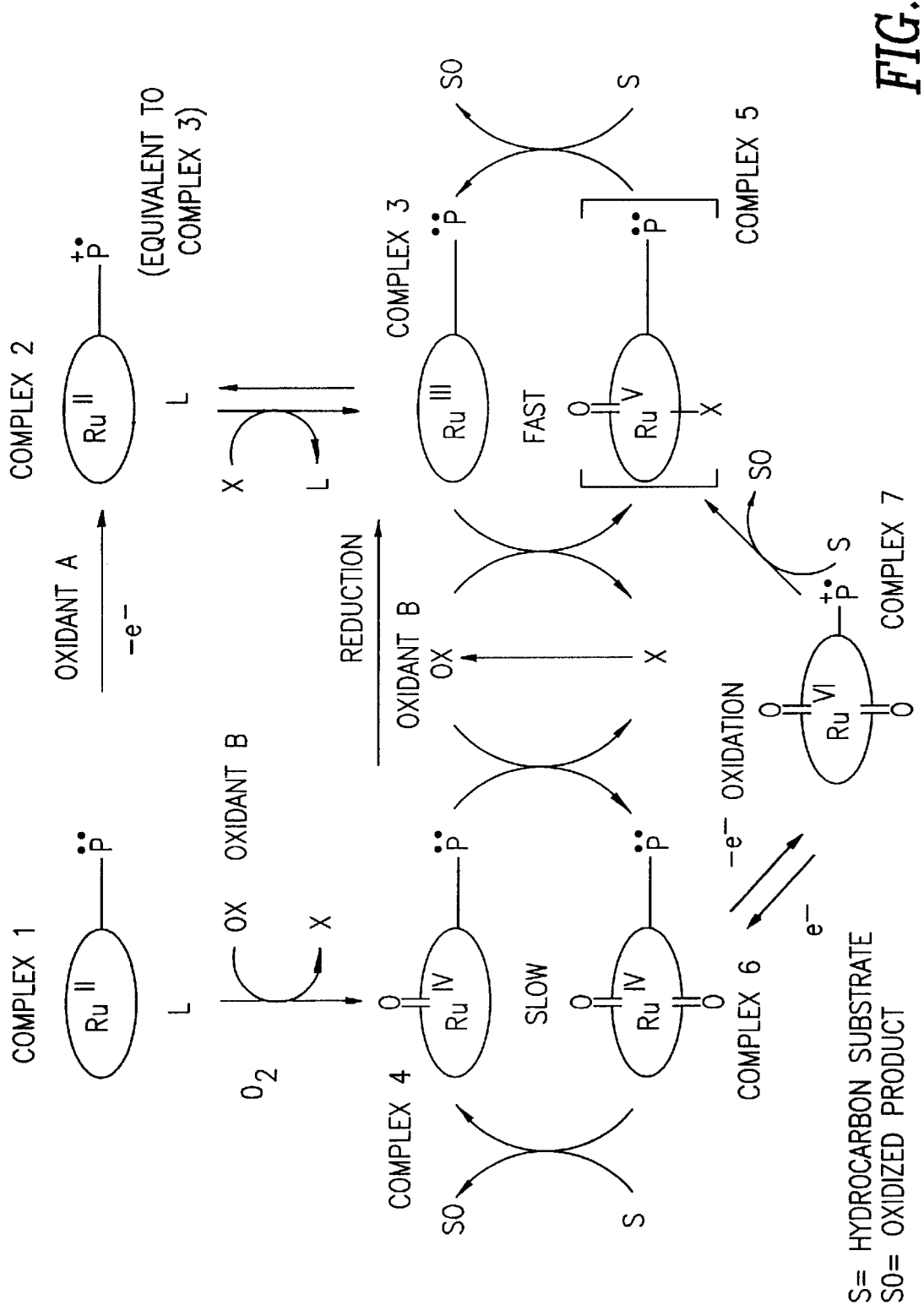
FIG. 1 is a schematic of the mechanistic pathways of obtaining the highly active $M^{III}$ porphyrin species using ruthenium as the metal center.

As a part of this discovery, it has also been found that several pathways exist for obtaining this active species. These pathways are best described by referring to FIG. 1 where the proposed mechanisms are illustrated using by way of example a ruthenium porphyrin. In FIG. 1, complex 1 shows as a starting material a ruthenium$^{II}$ porphyrin complex ($Ru^{II}$-P) having ligand axial "L". Axial ligand L can be a carbonyl group (CO), or a weakly coordinating ligand known in the art and/or commercially available, such as an alcohol, ether or acetonitrile. With the objective being the attainment of the highly active complex 3, $R^{III}$-P, there are at least three basic pathways which can be employed, each being useful in their own right depending upon the choice of oxidant and electron withdrawing substituent groups on the macrocyclic periphery. As stated previously, the presence of the peripheral electron withdrawing groups on the macrocycle serve to enhance the formation of the highly active species $M^{III}$.

Thus, in a first pathway, complex 2 is formed by adding an electron-removing oxidant A to complex 1. Complex 2 shows axial ligand L still present but the net charge on the porphyrin complex is now +1. This complex is an intermediate precursor to the highly active complex 3, $R^{III}$ porphyrin, and is in effect equivalent thereto since it quickly and autogenously loses axial ligand L under oxidation conditions in the presence of oxidant B to form complex 3 having the highly active $R^{III}$ species at its center. As depicted during the reaction from complex 2 to complex 3, the weakly coordinating axial ligand L is lost and is replaced by an appropriate counterion X which serves to coordinate the $R^{III}$ porphyrin complex. Counterion X may be any suitable counterion and may be present and part of the oxidant A solution or may be separately added thereto. Oxidant A may be selected from classes of organic and inorganic oxidants. Examples include N-oxides, peroxidic compounds, oxygen, air, periodates, $Fe^{III}$ perchlorate, triphenylamine cation radical, among others.

Oxidant B is an oxygen transfer oxidant and therefore differs in functions from oxidant A and must contain an oxygen. Examples of oxidant B materials include N-oxides, peroxidic compounds, oxygen, air and periodates, among others.

As an example of this first pathway, a methylene chloride solution of complex 1 is oxidized with solid $Fe\ (ClO_4)_3$ at room temperature under ambient conditions over 5–10 minutes to form a solution of complex 2 where x is $ClO_4$—. Conversion of complex 2 to the highly active complex 3 ($R^{III}$) can be accomplished by adding 1–5 equivalents of a pyridine-N-oxide. This transformation was complete in a few seconds and could be observed by a color change from green to orange. In the presence of 0.1–2M cyclohexane substrate(s) in $CH_2Cl_2$, cylohexanol to cyclohexanone products were produced as indicated in Table 1.

Alternatively, the active complex 3 can be generated in situ from complex 1 in a catalytic reaction mixture containing substrate S and oxidant B.

In a second pathway involving the formation of a highly active $M^{III}$ catalytic center, the same starting material, L—$Ru^{II}$ porphyrin (L—$Ru^{II}$-P) is used and oxidized using oxidant B. In this case, oxidant B differs in function from oxidant A in that oxidant B serves as an oxygen transfer agent and consequently must contain an oxygen atom available for such purpose. Complexes 4 and 6 are thus obtained by reacting complex 1 with oxidant B as shown. At this point continued oxidation forms the dioxo-$Ru^{VI}$-P which is known from U.S. Pat. 4,822,899 as being useful as a catalyst for hydrocarbons. As shown in FIG. 1, the oxidation of hydrocarbon substrate S to form oxidation product SO using this complex is slow. The present invention improves on the process described in the aforementioned '899 patent by taking complexes 4 and 6 and further reducing or oxidizing (third pathway) them respectively to ultimately generate the highly reactive metal species shown as $R^{III}$-P, (complex 3). In the case of complexes 4 and 6, ethanol will reduce complexes 4 and 6 to the highly active complex III species. In the case of complex 6, the removal of an electron via further oxidation with an electron removing oxidant such as oxidant A yields intermediate precursor complex 7 which readily converts to complex 5 and ultimately to the highly active species $R^{III}$ (complex 3).

It should be noted that although the above discussion has used ruthenium (Ru) as the metal, other metals such as those disclosed herein are also useful and can be substituted therefor. Likewise, although porphyrins and salens are the preferred coordination ligand, other ligands capable of generating the highly active species are contemplated.

What is evident from the above-mentioned descriptions of obtaining the $M^{III}$ active species, is that virtually inactive or exceptional slow metal species such as L—$Ru^{II}$-P, O=$Ru^{IV}$-P and diox-$Ru^{VI}$-P, i.e. the even metal oxidation states, can be converted into a highly active regenerative catalyst species which catalyzes the oxidation of hydrocarbon substrates (S) to their oxidation products (SO) selectively, efficiently and extremely rapidly when compared with the prior art.

It should be noted that the above discussion relating to the generation of the highly active $M^{III}$ species as the metal center must be considered in view of the electron withdrawing substituent groups on the periphery of the coordinating ligand, i.e. porphyrin or salen. In the first pathway of obtaining the $M^{III}$ species embodiment of the present invention, the periphery substituents may be various combinations of electron withdrawing groups which impede the formation or reformation of the dioxo- or oxo-ruthenium species. Halogen groups and nitro groups ($NO_2$) are examples of the preferred electron withdrawing groups.

The precatalyst complexes of the present invention from which the activated $M^{III}$ species is generated include the use of known complexes as well as novel porphyrin and salen complexes. As an example of a catalyst precursor complex 1 useful in the first pathway (described in FIG. 1) to obtaining the $M^{III}$ species, the following precatalyst porphyrin structure has been employed:

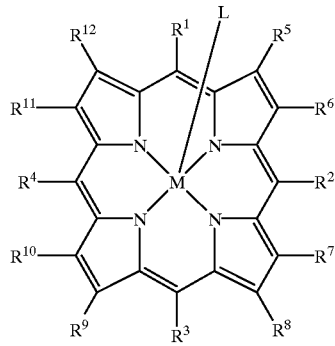

wherein axial ligand L is CO or a weakly coordinating ligand, such as an alcohol, ether or acetonitrile; $R^1$, $R^2$, $R^3$, $R^4$ may be the same or different and are haloalkyl $C_{1-20}$, haloaryl $C_{6-14}$, alkyaryl having a $C_{1-20}$ alkyl portion and a $C_{6-14}$ aryl portion; aryalkyl having a $C_{6-14}$ aryl portion and a $C_{1-20}$ alkyl portion; and haloalkylary and haloarylalkyl having the alkyl and aryl species containing $C_{1-20}$ and $C_{6-14}$ respectively; and $R^5$ through $R^{12}$ may be the same or different and may be H, Halo, —$NO_2$ or $R^1$, $R^2$, $R^3$ or $R^4$ as defined above.

The preferred starting material, i.e. catalyst precursor complex capable of generating the highly active species are [$Ru^{II}(O_2)$TPFPP] and [$Ru^{II}$TFPPX$_8$(CO)], where x is Cl or Br. For a discussion of the procedure for preparation of the starting material see Birnbaum et al., Inorg. Chem. 34 1751–1755, (1995), herein incorporated by reference.

Examples of highly active $Ru^{III}$-P catalysts obtained via the first pathway of FIG. 1 include:

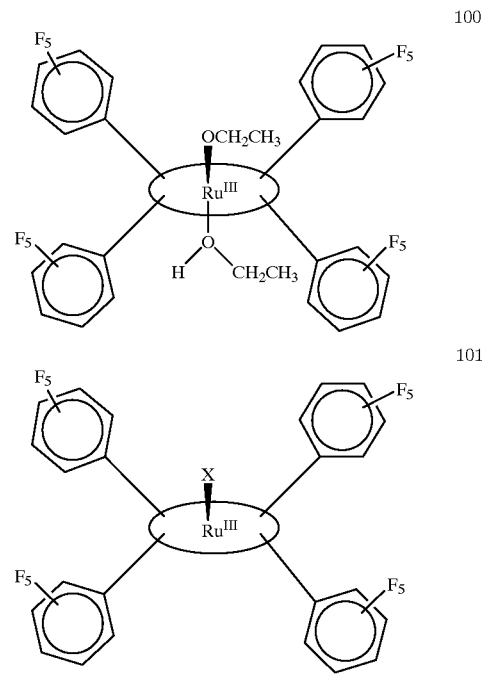

wherein X is $ClO_4^-$, $SbF_6^-$ or other suitable coordinating anion.

The metallosalen catalysts of the present invention are generally represented by the formula:

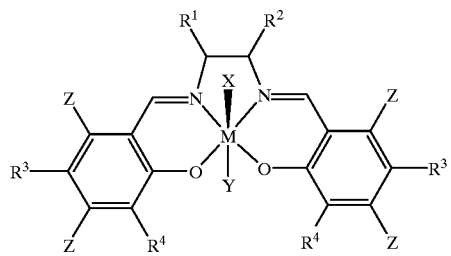

wherein $R^1$, $R^2$, $R^3$, $R^4$ may be the same or different and are selected from the group consisting of haloalkyl, haloaryl, alkaryl, aryalkyl, haloalkyaryl, haloaryalkyl where the alkyl portion has $C_{1-20}$ and the aryl portion has $C_{6-14}$; Z may be $R^{1-4}$, H, halogen or —$NO_2$; and X and Y may be the same or different and are CO, or a weakly coordinating ligand such as an alcohol, ether, acetonitrile and the like.

In the second pathway one can start with complex 6, complex 4 or the equivalent $Ru^{IV}$-P, and a reducing agent such a ethanol to produce the active $Ru^{III}$ species 100. Likewise, oxidation of complex 6 with oxidant A affords complex 7 which under the oxidative catalytic conditions described above forms complex 3 via complex 5. For example, oxidation of complex 6 with Fe ($ClO_4$)$_3$ would ultimately produce species 101 as the active catalyst, where x is a coordinating anion such as $ClO_4^-$, $SbF_6^-$ and the like.

In another embodiment of the present invention, a coordination ligand/transition metal complex having the structure

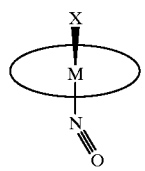

wherein M represents a transition metal selected from the group consisting of Ru, Os, Rh, Ir, Nb, Re, Tc and the standard Group VIB, VIIB and VIIIB metals of the periodic table, and X is a coordinating ligand.

Figure 2:
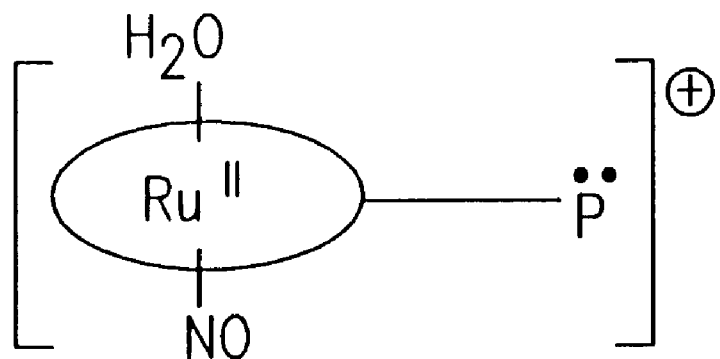
FIG. 2 is a schematic of the mechanistic pathway of obtaining the highly active $M^{III}$ species using ruthenium porphyrin containing nitrosyl (NO) as an axial ligand.
Figure 2:
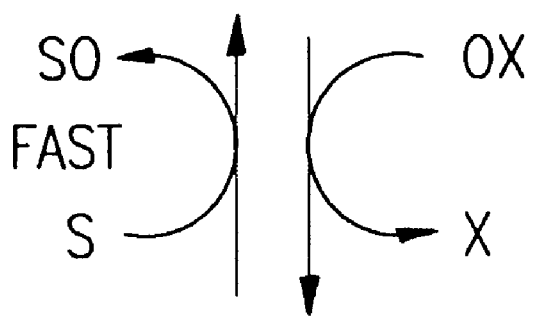
Figure 2:
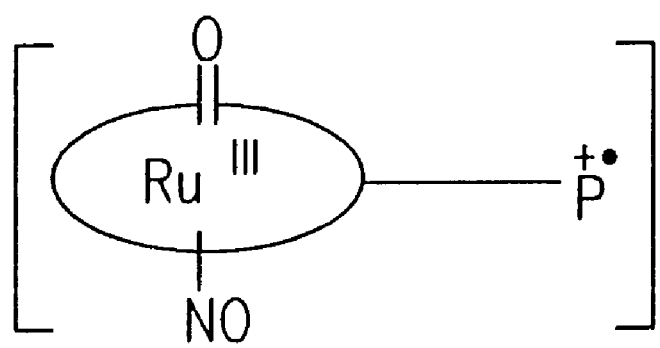
Figure 3:
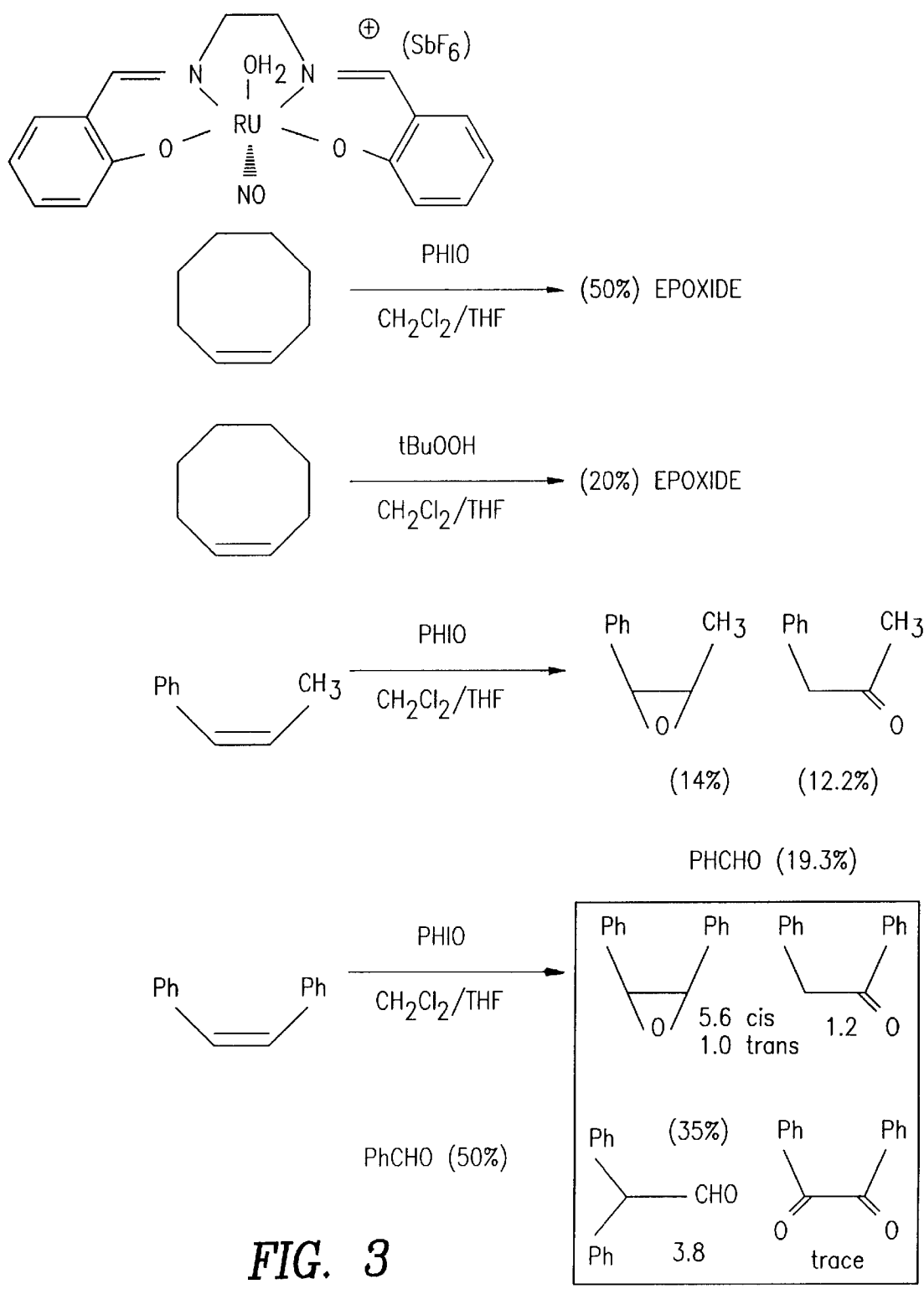
FIG. 3 is a schematic of catalytic oxidation of various hydrocarbons which were performed using a ruthenium salen complex containing an axial nitrosyl ligand.

The present invention also includes novel metalloporphyrin and metallosalen catalysts having a nitrosyl (N≡O) axial ligand which remains intact on the metal center, i.e. does not donate oxygen, during catalysis. These novel compounds also generate the highly activated species $M^{III}$-P as shown in FIG. 2. FIG. 2 shows the oxidation of $Ru^{II}$-P starting material having a nitrosyl axial ligand, with oxidant OX to generate the highly active species $R^{III}$-P. The oxidant used in this mechanism may be chosen from the same materials as oxidant A in FIG. 1. When the strong nitrosyl ligand is present, the highly active metal center species $[M—NO]^{+3}$ is maintained. When the peripheral substituents on the porphyrin or salen are electron withdrawing groups are also present, such a complex further enhances the activity of the $[M—NO]^{+3}$ species.

The metalloporphyrin catalysts having an axial nitrosyl ligand have the general structure:

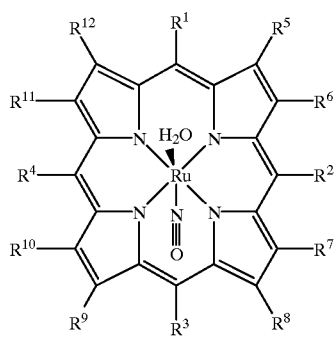

wherein $R^1$, $R^2$, $R^3$, $R^4$ may be the same or different and are haloalkyl $C_{1-20}$, haloaryl $C_{6-4}$, alkyaryl having a $C_{1-20}$ alkyl portion and a $C_{6-14}$ aryl portion; aryalkyl having a $C_{6-14}$ aryl portion and a $C_{1-20}$ alkyl portion; and haloalkylary and haloarylakyl having the alkyl and aryl species containing $C_{1-20}$ and $C_{6-14}$ respectively; and $R^5$ through $R^{12}$ may be the same or different and may be H, Halo, —$NO_2$ or $R^1$, $R^2$, $R^3$ or $R^4$ as defined above.

It should be mentioned that the above complex is paired with a suitable anion such as $SbF_6^{-1}$ or $ClO_4^-$ and the like. This holds true for other complexes discussed herein which require the same.

The preferred nitrosyl-containing metalloporphyrin catalyst is [Ru(TPFPP)(NO)($H_2O$)](SbF$_6$). This structure is shown below:

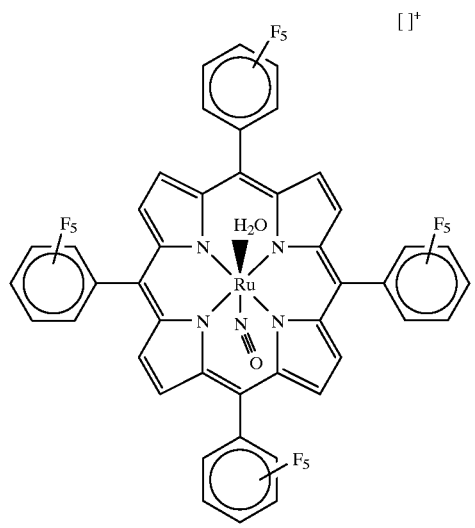

The nitrosyl-containing metallosalen catalysts of the present invention are generally represented by the formula:

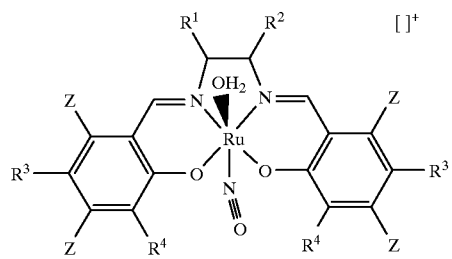

wherein $R^1$, $R^2$, $R^3$, $R^4$ may be the same or different and are selected from the group consisting of haloalkyl, haloaryl, alkaryl, aryalkyl, haloalkyaryl, haloaryalkyl where the alkyl portion has $C_{1-20}$ and the aryl portion has $C_{6-14}$; and Z may be $R^{1-4}$, H, halogen or —$NO_2$.

In the oxidation processes of the present invention, the catalyst is employed in a catalytic amount. Typically, the catalyst is present in molar ratios of catalyst to oxidizable substrate of about 1:100 to about 1:100,000, and preferably about 1:1000 to about 1:30,000. These ratios may vary depending on the specific catalyst and oxidizable substrate employed. The catalyst can be employed with or without a support.

As part of this invention, it has also been discovered that mixtures of catalyst complexes are useful. In particular, it has unexpectedly been discovered that certain catalyst complexes which are very slow to become activated can be mixed with those which are more easily oxidized, with the result being that activation of slower catalyst complex is triggered by the catalyst complex more easily oxidized.

Examples of olefins which can be epoxidized using the catalytic processes of the present invention include 1-octene, cyclooctene, styrene, β-methylstyrene, norborene, propylene, among numerous other. Mixtures of olefins are contemplated.

Examples of alkanes which can be oxidized to alcohols and further to their corresponding ketones include cyclohexane, n-hexane, decalin, among others. Mixtures of alkanes are contemplated.

Examples of aromatics which can be hydroxylated to alcohols and further to their corresponding quinones include benzene, naphthalene, chlorobenzene, among others. Mixtures of aromatics are contemplated.

The above classes of substrates can be employed in mixtures in the present invention. The oxidizing agent can be chosen from oxidants A and B as discussed above, depending on the starting material, the pathway chosen to obtain the highly active species and the reaction conditions.

The oxidant is supplied in an amount sufficient to allow the reaction to proceed. Typically, about 0.1 to about 40 moles and preferably about 0.5 to about 15 moles of oxygen is employed per mole of olefin double bond. These ratios also apply with respect to oxidation of alkanes and aromatics. Gaseous diluents such as carbon dioxide, nitrogen, noble gases and mixtures thereof may also be incorporated into the oxidants.

The reactions can be run at a wide range of temperature and pressure conditions. Reaction temperatures are generally from about room temperature to about 100° C., although temperatures outside of these ranges are operable. The preferred temperature range for practical purposes is about 65–70° C.

Reaction pressure conditions can also vary and be selected based on the reactants. Ambient pressure is generally suitable although slight pressure will assist the speed of reaction when oxidants such as air, pure oxygen or nitrous oxide are employed. In such cases, pressures of about 0.5 to about 4.0 atmospheres are employed.

The following examples are given to illustrate the present invention and are not to be construed as limiting the effective scope of the invention.

EXAMPLES

A preferred catalyst precursor species used to form the $M^{III}$ active species of the present invention is carbonyl (5,10,15,20-tetrapentafluorophenylporphyrinato) ruthenium (II), hereinafter abbreviated as [$Ru^{II}$(TPFPP)(CO)].

Catalyst precursor complex 1 (FIG. 1) was prepared by metallation of the free base with $Ru_3$ $(CO)_{12}$ in refluxing o-diclorobenzene. A 55% yield of the catalyst was obtained. For similar preparation details see Murashashi, S. I., et al., Tetrahedron Lett., 1995, 35, 8059–8062.

Catalyst precursor complex 1 was then used for the catalytic oxygentation of a number of hydrocarbon substrates. The chosen substrates and the oxygenated product yields and turnover rates are shown in Table I, below.

TABLE I

Hydrocarbon oxidation[a] catalyzed by catalyst precursor [$Ru^{II}$(TPFPP)(CO)] in the presence of $pyCl_2NO$ in dichloromethane at 65° C.

| Exper. No. | Substrate | Time (Min) | Product | (% conv.)[b] | Yield[c] (%) | Max rate[d] (T.O./min) |
|---|---|---|---|---|---|---|
| 1[e] | adamantane | 20 | 1-adamantanol | (76.2) | 91 | 72 |
|  |  |  | adamantane-1,2-diol | (7.3) |  |  |
| 2[f] | adamantane | 120 | 1-adamantanol | (61.0) | 97 | 800 |
|  |  |  | adamantane-1,3-diol | (6.0) |  |  |
| 3 | cis-decalin | 25 | (Z)-9-decalol | (79.6) | 90 | 64 |
|  |  |  | (Z)-decal-9,10-diol | (4.2) |  |  |
| 4 | trans-decalin | 60 | (E)-9-decalol | (25.8) | 70 | 4.4 |
|  |  |  | secondary alcohols | (4.3) |  |  |
|  |  |  | ketones | (13.9) |  |  |
| 5[f] | cyclohexane | 180 | cyclohexanol | (1.6) | 95 | 22 |
|  |  |  | cyclohexanone | (6.7) |  |  |
| 6 | 1-octene | 60 | 1,2-epoxyoctane | (96.0) | 96 | 11 (36) |
| 7 | 1-octene/ adamantane | 60 | 1,2-epoxyoctane 1-adamantanol | (54.0) (28.0) | 90 | 9.5 |
| 8[h] | benzene | 12h | 1,4-benzoquinone | (13.3) | 40 | — |

[a][substrate] = [$pyCl_2NO$] = 0.02 M, [complex 1] = 50 $\mu$M.
[b]percent conversion based on the amount of substrate reacted. Products were identified by GC-MS and compared to authentic samples.
[c]percent yield based on $pyCl_2NO$.
[d]maximum oxidation rate measured as the slope of the zero order phase in the kinetic plot.
[e]similar conversions were obtained with catalyst precursors [$Ru^{VI}$(TPFPP)$O_2$], and [$Ru^{VI}$(TPFPBr$_8$P)$O_2$]
[f][substrate] = [$pyCl_2NO$] = 0.2 M, [complex 1] = 10 $\mu$M.
[h][benzene] = 2M, [$pyCl_2NO$] = 0.02 M, [complex 1] = 50 $\mu$M.

Catalyst precursor complex 1 was reacted with 2,6-dichloropyridine-N-oxide, hereinafter [$pyCl_2NO$], as the oxygen donor. The hydoxylations of adamantane and cis-decalin were achieved with high selectivity, complete stereoretention, high rate, i.e., up to 800 turnovers/minute, and high efficiency (see Experiment #'s 1–3). Oxygenation of less reactive substrates also proceeded with significant turnover numbers.

Analysis of the adamantane hydroxylation catalyzed in the presence of catalyst precursor 1 proved revealing information with respect to the mechanism of this process. The evolution of products over time (Curve A, FIG. 5) showed an initial induction period followed by a fast, zero-order phase with maximum rate and the highest efficiencies (column 6, Table 1). Deviation form linear behavior was observed after 90% oxygen donor had been consumed. Recharge of the reaction mixture with $pyCl_2NO$ and adamantane afforded another catalytic burst with a similar rate but with no induction period (Curve B, FIG. 5). Thus, the catalyst was still present in a fully active form.

The initial step in the sequence of transformations leading from catalyst precursor 1 to the actual active catalyst was the formation of an adduct 1a (not shown) [K=350M$^{-1}$, at 25° C.], as detected by a red-shift of the Soret band from 404 nm in precursor 1 to 406 nm in the UV spectrum of adduct 1a. Moreover, photo-stimulation and reduction of the induction period was observed with red-orange light (>560 nm).

Ruthenium porphyrin radical cations are known to be formed from the corresponding carbonyl compounds by chemical or electrochemical oxidation. See Barley, M.; Becker, J. Y.; Domazetis, G.; Dolphin, D.; James, B. R. *Can. J. Chem.* 1983, 61, 2389–2396. Further, these species show a characteristic absorption band in the 600–700 nm region. See Dolphin D.; James, B R.; Leung, T. *Inorg. Chim. Acta.* 1983, 79, 25–27; Leung, T.; James, B. R,; Dolphin, D. *Inorg. Chim. Acta* 1983, 79, 180–181. The radical cation complex 2 was quantitatively generated by reaction of catalyst precursor complex 1 with ferric perchlorate. This reaction involved making a dichloromethane solution of the catalyst complex 1 and passing it through a small column packed with Fe $(ClO_4)_3 \cdot nH_2O$. An emerald green solution was obtained, which was stable at −50° C. IR analysis ($CH_2Cl_2$, $cm^{-1}$) showed the expected absorbance of C=O at 1979 $cm^{-1}$. The shift of v-CO (from 1950 to 1979 $cm^{-1}$), the broadening of the Soret band, the appearance of a 635 nm absorption (FIG. 2, dotted curve), and the EPR signal (g=2.00) (FIG. 2, inset a) agree with the proposed structure for complex 2. Dichloromethane solutions of complex 2 were stable at low temperature, but complex 2 converted slowly to catalyst precursor complex 1 on standing at 24° C. as monitored by IR or UV spectroscopy with clear isobestic behavior.

Figure 4:
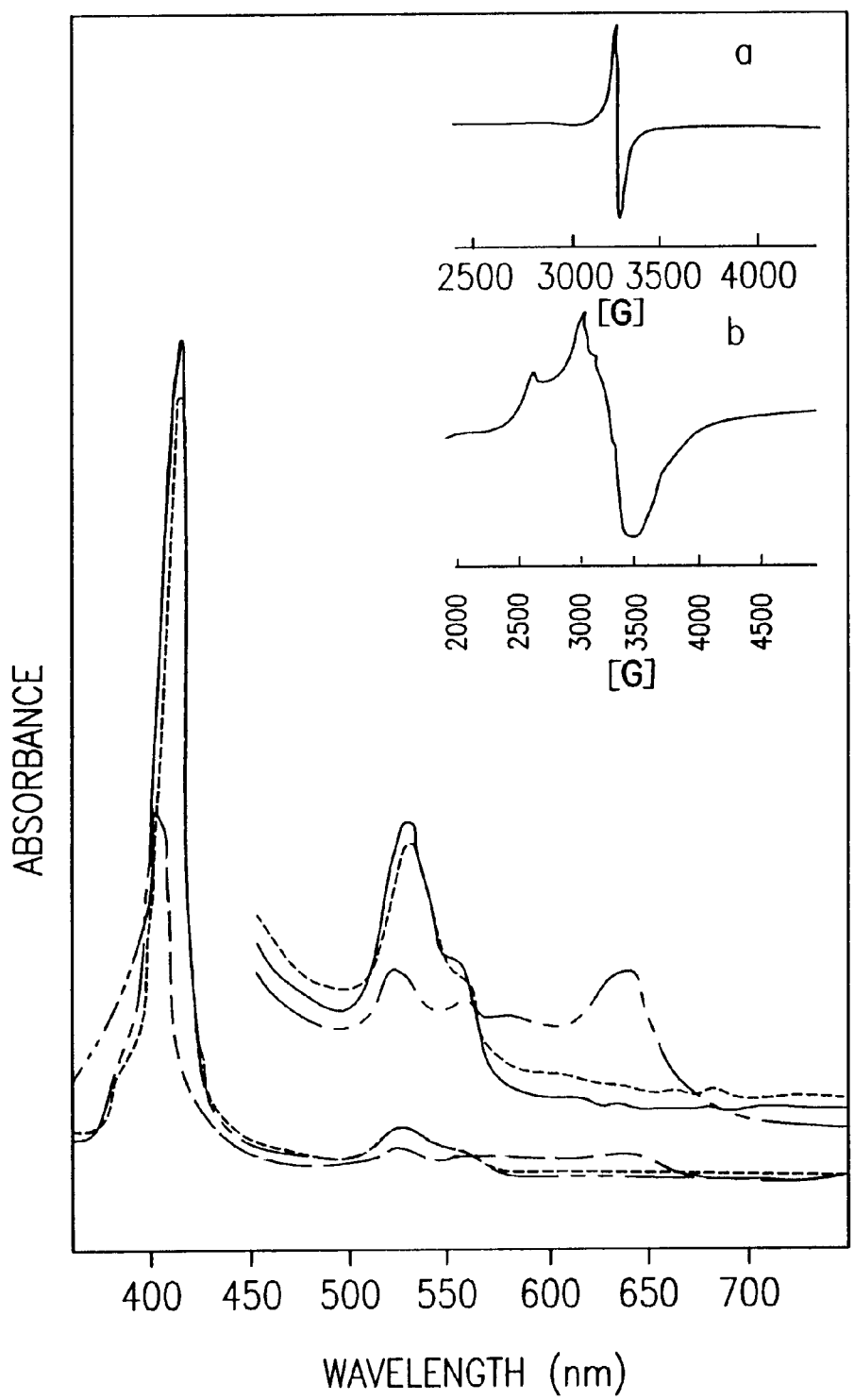
FIG. 4 shows the UV spectra of the $M^{III}$ highly active catalyst species of the present invention.
Figure 5:
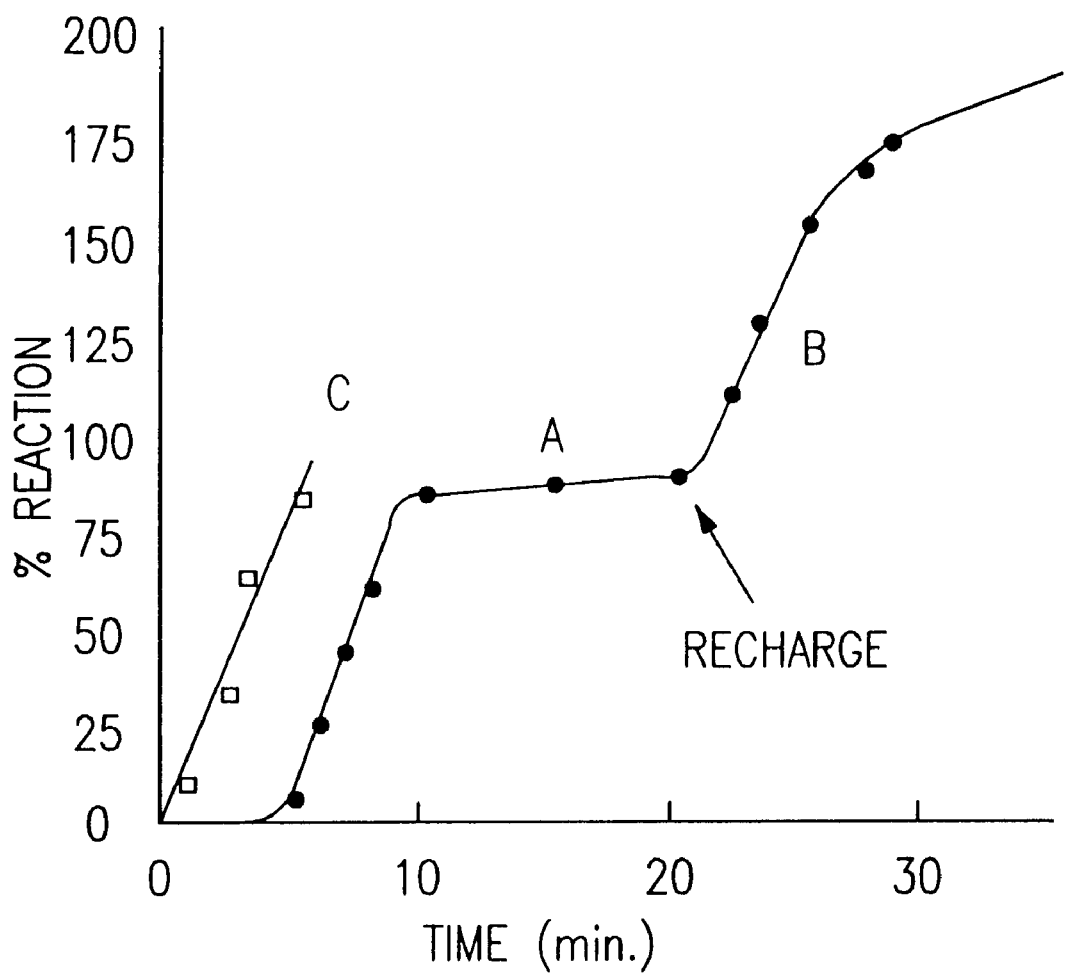
FIG. 5 is a graph of percent reaction vs. time for hydroxylation of adamantine by a catalyst of the present invention.

When a solution of complex 2 was allowed to react with an excess of the N-oxide at −50° C., the color of the solution turned from green to orange. Evolution of CO was observed as the solution reached 25° C. leading to species complex 3 (FIG. 4, line-dotted curve). The occurrence of an internal electron transfer process from ruthenium (II) to the porphyrin radical cation upon ligation has been reported by Dolphin et al. See Barley, M.; Dolphin D.; James, B. R.; *J.C.S. chem. Commun.* 1984, 1499–1500; Barley, M.; Becker, J. Y.; Domazetis, G.; Dolphin, D.; James, B. R. *J.C.S. Chem. Commun.* 1987, 982–983. Indeed, compound 3b (not shown) (OD=2,6 -lutidine-N-oxide) showed an EPR signal typical of a ruthenium (III) species. See James, B. R.; Dolphin, D.; Leung, T. W.; Einstein, F. W.; Willis, A. C. *Can. J. Chem.* 1984, 62, 1238–1245. (e) James, B. R.; Mikkelsen, S. (FIG. 4, inset b, g⊥=2.55, g//=2.05). Significantly, complex 3 (OD=$pyCl_2NO$) catalyzed adamantane hydroxylation with no induction period. The typical reaction procedure is modified by treating first the solution of catalyst precursor complex 1 with Fe $(ClO_4)_3 \cdot nH_2O$ followed by the amount of $pyCl_2NO$ at −50° C. The substrate was added after complex 3 formed at 25° C. The reaction mixture was then heated to 65° C. However, the zero-order regime occurred with a similar rate (FIG. 5, curve C). Moreover, complex 3 was the species observed by UV spectroscopy during the rapid phase of catalysis.

On the basis of the above observations, the catalytic cycle in FIG. 1 is proposed for this reaction. Such a mechanism accounts both for the slow intiation leading to the formation of complex 3 and for the zero-order phase of the oxygenation process. Significantly, the hydroxylation of adamantane showed a kinetic deuterium isotope effect (kH/kD= 3.05) in a competitive experiment while deuterated and undeuterated substrates displayed the same zero-order fast kinetic phase in separate reactions. This observation can be explained if a reactive intermediate, complex 5, is formed in the rate determining step. The temperature dependence of adamantane hydroxylation indicates a ΔH‡ of 28.6 kcal/mol for this process. An Eyring plot of the zero order rate constants determined over the range 318–338K was linear (In k=9.73, −10.76, −12.39 at 338, 328 and 318K, respectively).

The unusually low reactivity of 1-octene with respect to adamantane and cisdecalin was found to be due to catalyst inhibition by this substrate. Thus, 1-octene was twice as reactive as adamantane in competitive oxidation and the efficiency of the 1-octene epoxidation was improved threefold when excess $pyCl_2NO$ was employed. Table 1, Exp. #6 shows a maximum rate of 36 turnovers per minute. The respective molar concentration of reactants in $CH_2Cl_2$ at 65° C. was [1-octene]=0.01M, [$pyCl_2NO$]=0.04M and [catalyst precursor complex 1]=50 μM. On this basis coordination of 1-octene to the $R^{III}$ center is implicated. See Groves, J. T.; Ahn, K. H.; Quinn, R. *J. Am. Chem. Soc.* 1988,110, 4217–4220.

All of the results are consistent with the rate-determining oxidation of $R^{III}$ species to a $Ru^V$-oxo species. The intermediacy of [$Ru^{VI}(TPFPP)(O_2)$] is unlikely since no products were observed upon spontaneous decomposition of [$Ru^{VI}(TPFPP)(O_2)$] in the presence of adamantane. Oxygen donors such as iodosylbenzene, magnesium monoperoxyphtalate, oxone and tetrabutylammonium periodate were able to produce the trans-dioxo species.

The above experiments show that rapid, efficient hydrocarbon oxygenation can be achieved with catalysts of the present invention, and in particular with a perfluorophenyl $Ru^{III}$ porphyrin catalyst via the stepwise oxidation of the ruthenium(II) carbonyl complex. The results suggest that a highly reactive $Ru^V$-oxo porphyrin intermediate, or its equivalent, is formed in the rate determining step of catalysis.

FIG. 4 shows superimposed UV spectra ($CH_2Cl_2$,25° C.) of catalyst species 1a (not shown), and complexes 2 and 3. The inset shows x-band EPR of complex 2 (inset a) and complex 3 (inset b) recorded in $CH_2Cl_2$, at 135K. The active catalytic species complex 3 ($Re^{III}$) is represented on inset b.

FIG. 5 shows % reaction vs. time plot for adamantane hydroxylation by catalyst precursor complex 1 in the presence of $pyCl_2NO$ in $CH_2Cl_2$ at 65° C. Adamantane (0.02 mmoles), $pyCl_2NO$ (0.02 mmole), catalyst precursor complex 1 (50 μmole). Curve A: typical kinetic trance with catalyst percursor complex 1. This curve shows the loss of CO from the catalyst precursor species, where ligand x=CO. Curve B: the reaction A is recharged with $pyCl_2NO$ (0.02 mmol) and adamantane (0.02 mmol) at t=20 min. Curve C: Complex 3 was recycled and used as the catalyst. In view of the high number of turnovers, it was totally unexpected that recycling of the catalyst would be possible.

The following examples demonstrate the effectiveness of the $R^{III}$ porphyrin catalytic complexes having an axial nitrosyl ligand and fluorinated phenyl groups on the porphyrin periphery. The active catalyst species is generated from [$Ru(TFPP)(NO)(H_2O)$]$^{1+}$ as described below.

A solution containing 1M cyclohexane, 0.625M 2,6-dichloropyridine N-oxide and 0.10 mM [$Ru(TPFPP)(NO)(H_2O)$]($SbF_6$) in 1 ml $d_6$-benzene was heated for eight hours in a sealed tube at 75° C. affording high yields of oxidized products. A combined yield of 93% and 1500 catalytic turnovers were obtained of two products, cyclohexanone and cyclohexanol (mole ratio 4:1). In $CD_2Cl_2$ the same reaction conditions proceeded to give 5600 turnovers to generate cyclohexanone and cyclohexanol (8:1) in a combined 98% yield in twelve hours. 2,6-dichloropyridine-N-oxide was unable to hydroxylate cyclohexane by heat alone as shown by a control experiment, proving that the ruthenium complex must be present to effect reaction.

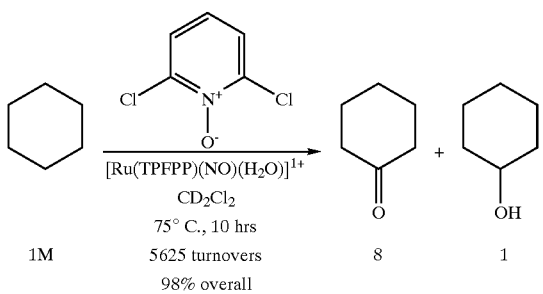

Adamantane was oxidized at a rate of at least 50 turnovers per minute as determined by H NMR spectroscopy. Up to 6000 turnovers of adamantane oxidation were obtained in three hours in d6-benzene, with a mixture of 1-adamantanol (85%), 2-adamantanol (1%), 1,3-adamantanediol (5%) and 2-adamantanone (0.5%) produced. No obvious deterioration of catalyst occurred over time. Decrease in the concentration of catalyst to 0.010 mM provided up to 26000 turnovers of oxidation in a 12 hour period with similar selectivity (83% 1-adamantanol, 1.6% 2-adamantanediol, 4% 1,3 adamantanediol, 0.5% 2-adamantanone. The solvent, $d_6$-benzene, was relatively inert to oxidation by the catalyst as shown by the lack of oxidant consumption (less than 10%) after 12 hours reaction at 75° C. in the absence of substrate. Oxidations of alkanes were much slower at room temperature as mentioned in the preceding section, with 50 turnovers of adamantane oxidation obtained over an 8 hour period in $CD_2Cl_2$. A summary of results of the oxidation of alkanes by the ruthenium nitrosyl/N-oxide oxidation system at high temperature can be found in Table II. Yields in most instances were good to excellent, and turnover numbers were high. [Ru(TMP)(NO)($H_2O$)](SbF$_6$) and [Ru(TDCPP) (NO)($H_2O$)](SbF$_6$) were found to be effective oxidation catalysts, although not nearly as efficient as [Ru(TPFPP) (NO)($H_2O$)](SbF$_6$) in the oxidation of alkane substrates.

Olefin substrates were also readily epoxidized by the high temperature [Ru(TPFPP)(NO)($H_2O$)](SbF$_6$) /N-oxide oxidation system. An excess of 4800 turnovers was obtained in the epoxidation of methylene cyclohexene over a 12 hour period in a 92% yield versus consumed oxidant. Unreactive olefinic substrate methyl acrylate was slowly epoxidized by the catalyst system in 70 turnovers and 35% yield in a 12 hour period. In the absence of catalyst the , βepoxymethylacrylate could not be obtained nor was oxidant decomposed. Hence, uncatalyzed β-conjugate addition of the N-oxide to the olefin was not responsible for the observed epoxide yield. Cyclohexene was an interesting substrate at high temperature. In contrast to the high selectivity of the room temperature oxidation (95% cyclohexene oxide, 5% cyclohexenol) the high temperature oxidation was relatively non-selective (59% cyclohexene oxide and 39% cyclohexenol, 98% overall). Indeed, the reaction of cyclohexane proceeded to give predominantly ketone (4:1) whereas in this case, the reaction of alcohol to ketone was not observed. Adamantane oxidation also provides a small amount of the 2-ketone with respect to the 2-alcohol (0.5% versus 1%).

TABLE II

Oxidations of alkanes by [Ru(TPFPP)(NO)($H_2O$)](SbF$_6$) and 2,6-dichloropyridine N-oxide in $d_6$-Benzene at 75° C.[a]

| Substrate[b] Oxidant[b] Catalyst[b] | Substrate[c] | Products,[d] Yield[e] and Turnovers[f] | Reaction Time (hr) | Turnover Rate[g] |
|---|---|---|---|---|
| 1.0 0.625 $1.0 \times 10^{-4}$ | cyclohexane | 75.3% cyclohexanone (1215) 18.7% cyclohexanol (280) (4:1 ketone:alcohol- 93% overall) (Total catalytic turnovers: 1500) | 12 | 5 |
| 1.0 0.625 $1.0 \times 10^{-4}$ | cyclohexane[h] | 87.7% cyclohexanone (2468) 10.8% cyclohexanol (611) 8:1 ketone:alcohol- 98% overall) (Total catalytic turnovers: 5625) | 12 | 8 |
| 1.0 0.625 $1.0 \times 10^{-4}$ | adamantane | 85% 1-adamantanol (5688) 1.0% 2-adamantanol (62) 5.0% 1,3 adamantane diol (312) 0.5% adamantanone (31) | 3 | 50 |
| 1.0 0.625 $1.0 \times 10^{-5}$ | adamantane | 83% 1-adamantanol (25937) 1.6% 2-adamantonal (500) 4.0% 1,3 adamantane diol (1250) 0.5% Adamantanone (156) | 12 | 50 |
| 1.0 0.050 $1.0 \times 10^{-3}$ | adamantane[i] | 68% adamantanol (340) | 4 | 2.5 |
| 1.0 0.02 $1.0 \times 10^{-3}$ | adamantane[j] | 49% adamantanol (100) | 12 | 0.28 |
| 1.0 1.1 (IO$_4^-$) | adamantane | 91%[k] adamantanol (250) 9%[k] adamantanone (25) | 8 | N.D. |

[a]All reactions were performed with and without catalyst. Controls gave low yields generally 0%.
[b]Concentration in M.
[c]All substrates were chromatographed on basic alumina before use.
[d]Products were determined by comparison to authentic standards and by $^1$H NMR, GCMS and GC assay.
[e]Yields are expressed versus consumed oxidant.
[f]Turnover numbers are expressed an mmol product formed per mmol catalyst.
[g]Rate is in turnover per minute.
[h]Reaction was run in 1 ml $CD_2Cl_2$ at 75° C.
[i]Catalyst was [Ru(TDCPP)(NO)($H_2O$)](SbF$_6$).
[j]Catalyst was [Ru(TMP)(NO)($H_2O$)](SbF$_6$).
[k]Yields are relative to total product formed, not oxidant consumed.

TABLE III

Oxidations of alkanes by [Ru(TPFPP)(NO)($H_2O$)](SbF$_6$) and 2,6-dichloropyridine N-oxide in $d_6$-Benzene at 75° C.[a]

| Substrate[b] Oxidant[b] Catalyst[b] | Substrate[c] | Products,[d] Yield[e] and Turnovers[f] | Reaction Time (hr) | Turnover Rate[g] |
|---|---|---|---|---|
| 1.0 0.625 $1.0 \times 10^{-4}$ | methylene cyclohexane | 92% methylene cyclohexane oxide (4812) | 12 | 10 |

TABLE III-continued

Oxidations of alkanes by [Ru(TPFPP)(NO)(H₂O)](SbF₆) and 2,6-dichloropyridine N-oxide in d₆-Benzene at 75° C.[a]

| Substrate[b] Oxidant[b] Catalyst[b] | Substrate[c] | Products,[d] Yield[e] and Turnovers[f] | Reaction Time (hr) | Turnover Rate[g] |
|---|---|---|---|---|
| 1.0 | cyclohexene | 59% cyclohexane oxide (140) | 2 | 2.0 |
| 0.25 | | 39% cyclohexenol (91) | | |
| 5.0 × 10⁻⁴ | | (98% overall) | | |
| 1.0 | 1-octene | 84% 1,2 epoxyoctane (420) | 2 | 10 |
| 0.25 | | | | |
| 5.0 × 10⁻⁴ | | | | |
| 1.0 | methyl acrylate | 35% epoxide (70) | 12 | 0.125 |
| 0.25 | | | | |
| 5.0 × 10⁻⁴ | | | | |
| 1.0 | cyclooctene | 95% cycloctene oxide (475) | 2 | 4 |
| 0.25 | | | | |
| 5.0 × 10⁻⁴ | | | | |

[a]All reactions were performed with and without catalyst. Controls gave low yields generally 0%.
[b]Concentration in M.
[c]All substrates were chromatographed on basic alumina before use.
[d]Products were determined by comparison to authentic standards and by ¹H NMR, GCMS and GC assay.
[e]Yields are expressed versus consumed oxidant.
[f]Turnover numbers are expressed as mmol product formed per mmol catalyst. Reaction conditions: 0.5 mM[Ru(TPFPP)(NO)(H₂O)](SbF₆), 0.25 M (500 equivalents) dichloropyridine N-oxide, 1 ml d₆-benzene, 1 M substrate were added in a sealed tube and heated at 75° C. for the time stated in the table.

By way of example of the use of mixtures of catalysts, the following experiment was conducted to demonstrate the use of an easily oxidized catalyst precursor to trigger the oxidation of a slower catalyst precursor complex. Porphyrin activation studies using the following procedure was conducted.

The activation of $Ru^{II}(CO)TPFPPBr_8$ ($1.0\times10^{-5}$M) in $CH_2Cl_2$ at 65° C. with 2,6- dichloropyridine-N-oxide (0.020M) in the absence of substrate was followed by the UV/vis spectroscopy. The sharp drop of the Soret absorbance of the porphyrin (430 nm), indicating the activation, was detected at 30 minutes. Interestingly, when the concentration of 2,6-dichloropyridine-N-oxide is high (0.20M), typical of catalytic conditions, $Ru^{II}(CO)TPFPPBr_8$ cannot be activated even after prolonged heating. When a mixture of $Ru^{II}(CO)TPFPPBr_8$ ($1.0\times10^{-5}$M) and a small amount of $Ru^{II}(CO)TPFPP$ ($1.0\times10^{-6}$M) was employed, the activation time of the brominated porphyrin dropped to 7.5 min. $Ru^{II}$ goes to $R^{III}$ and triggers the bromine-containing less active catalyst precursor. This value coincides with $t_{activation}$ of $Ru^{II}(CO)TPFPP$ ($1.0\times10^{-6}$M) alone under the same conditions observed by monitoring the maximum of its Soret 408 nm. Therefore, a small dope of more reactive porphyrin can trigger the activation of less active one.

What is claimed is:

1. A method of catalyzing the oxidation of hydrocarbons comprising contacting in the presence of an oxidant under reaction conditions said hydrocarbon with a metallo macrocyclic catalyst complex selected from the group consisting of porphyrins, salens, and mixtures thereof, said catalyst complex having both electron withdrawing substituents on its periphery, and an internal ligand set selected to maximize the catalytic activity of the catalytic metal contained within and to prevent reversion to a stable even oxidation state, said catalytic metal comprising a $Ru^{III}$ species formed in situ from a stable catalyst precursor complex having the structural formula

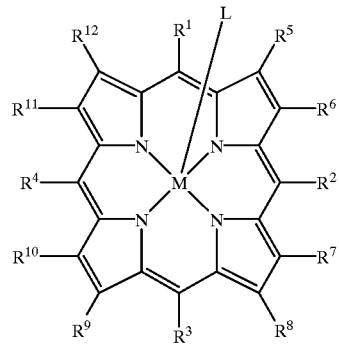

wherein axial ligand L is CO or a weakly coordinating ligand; $R^1$, $R^2$, $R^3$, $R^4$ may be the same or different and are haloalkyl $C_{1-20}$, haloaryl $C_{6-14}$, alkyaryl having a $C_{1-20}$ alkyl portion and a $C_{6-14}$ aryl portion; aryalkyl having a $C_{6-14}$ aryl portion, and a $C_{1-20}$ alkyl portion; and haloalkylary and haloaryalkyl having the alkyl and aryl species containing $C_{1-20}$ and $C_{6-14}$ respectively; and $R^5$ through $R^{12}$ may be the same or different and may be H, Halo, —$NO_2$, or $R^1$, $R^2$, $R^3$, or $R^4$; and wherein Ru is in an even oxidation state.

2. A method of claim 1, wherein the following stable catalyst precursor complex is substituted for the formula of claim 1:

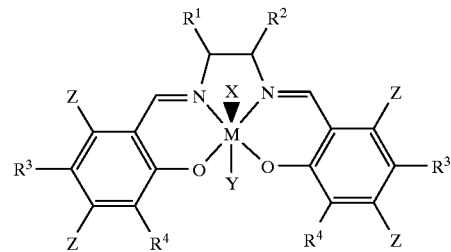

wherein $R^1$, $R^2$, $R^3$, $R^4$ may be the same or different and are selected from the group consisting of haloalkyl, haloaryl, alkaryl, aryalkyl, haloalkyaryl, haloaryalkyl where the alkyl portion has $C_{1-20}$ and the aryl portion has $C_{6-14}$; Z may be $R^{1-4}$, H, halogen or —$NO_2$; and X and Y may be the same or different and may be CO or a weakly coordinating ligand.

3. The method of claim 1 wherein said highly activated complex is one of

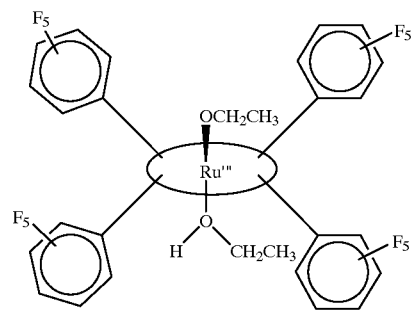

-continued

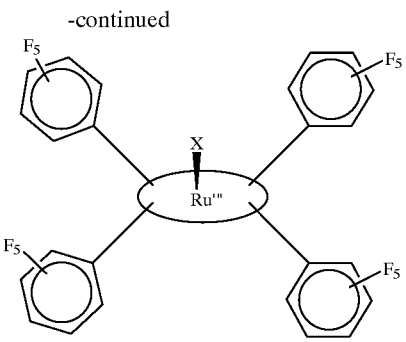

wherein X is a coordinating anion and ⌒ represents a porphyrin or salen complex.

4. A method of catalyzing the oxidation of hydrocarbons using high activity porphyrin metal complexes which includes the steps of:
(I) providing a coordinating ligand having electron-withdrawing substituent groups on its periphery and containing within it a low activity metallic species selected from the group consisting of dioxo-$Ru^{VI}$, $XY-Ru^{IV}$, and $Z-Ru^{II}$;
(ii) reducing or oxidizing said low activity metallic species with a suitable reducing or oxidizing agent to obtain a $Ru^{III}$ species or its equivalent which is less stable relative to said low activity metallic species;
(iii) contacting said $Ru^{III}$ species or its equivalent with said hydrocarbon in the presence of an oxidant to effectuate said catalysis of said hydrocarbons, wherein X and Y may be the same or different and are oxygen or a halogen, and Z is CO or a weakly coordinating ligand.

5. The method of claim 4 wherein said reducing is performed with an oxidizing agent selected from the group consisting of organic and inorganic oxidants.

6. The method of claim 5 wherein said oxidizing agent is selected from the group consisting of N-oxides, peroxidic compounds, oxygen, air, periodates, $Fe^{III}$ perchlorate, triphenylamine cation radical and mixtures thereof.

7. The method of claim 4 wherein said oxidizing is performed with an oxygen transfer agent containing an oxygen atom.

8. The method of claim 7 wherein said oxidizing is performed with an agent selected from the group consisting of N-oxides, peroxidic compounds, oxygen, air, periodates and mixtures thereof.

9. The method of claim 4 wherein the electron-withdrawing substituent groups are selected from the group consisting of haloalkyl $C_{1-20}$, haloaryl $C_{6-14}$, alkyaryl having a $C_{1-20}$ alkyl portion and a $C_{6-14}$ aryl portion, aryalkyl having a $C_{6-14}$ aryl portion and a $C_{1-20}$ alkyl portion, and haloalkylary and haloarylakyl having the alkyl and aryl species containing $C_{1-20}$ and $C_{6-14}$ respectively, halo, and —$NO_2$.

10. The method of claim 4, wherein the $Ru^{III}$ species are

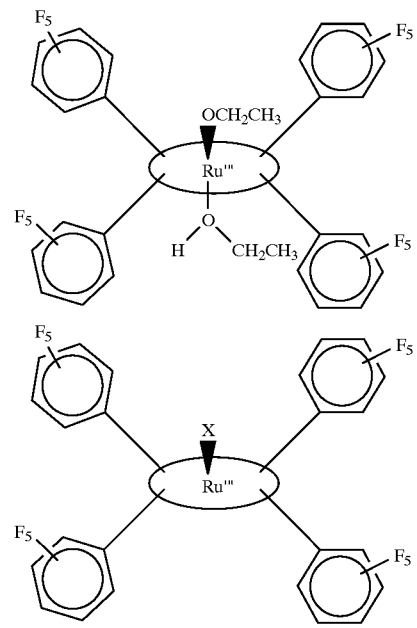

wherein X is a coordinating anion and ⌒ represents a porphyrin or salen complex.

* * * * *

UNITED STATES PATENT AND TRADEMARK OFFICE
CERTIFICATE OF CORRECTION

PATENT NO. : 6,002,026
DATED : December 14, 1999
INVENTOR(S) : Groves et al.

It is certified that error appears in the above-indentified patent and that said Letters Patent is hereby corrected as shown below:

At column 5, line 59, the printed patent incorrectly reads "species such as $R^{III}$". The patent should read --species such as $Ru^{III}$--.

At column 5, line 61, the printed patent incorrectly reads "its equivalent, e.g. $R^{III}$". The patent should read --its equivalent, e.g. $Ru^{III}$--.

At column 6, line 7, the printed patent incorrectly reads "attainment of the highly active complex 3, $R^{III}$-P". The patent should read --attainment of the highly active complex, $Ru^{III}$-P--.

At column 6, line 19, the printed patent incorrectly reads "precursor to the highly active complex 3, $R^{III}$". The patent should read --precursor to the highly active complex 3, $Ru^{III}$--.

At column 6, line 23, the printed patent incorrectly reads "having the highly active $R^{III}$". The patent should read --having the highly active $Ru^{III}$--.

At column 6, line 27, the printed patent incorrectly reads "$R^{III}$". The patent should read --$Ru^{III}$--.

At column 6, line 44, the printed patent incorrectly reads "($R^{III}$)". The patent shouldr ead --($Ru^{III}$)--.

UNITED STATES PATENT AND TRADEMARK OFFICE
CERTIFICATE OF CORRECTION

PATENT NO. : 6,002,026
DATED : December 14, 1999
INVENTOR(S) : Groves et al.

It is certified that error appears in the above-indentified patent and that said Letters Patent is hereby corrected as shown below:

At column 7, line 3, the printed patent incorrectly reads "highly reactive metal species shown as $R^{III}$-P". The patent should read --highly reactive metal species shown as $Ru^{III}$-P--.

At column 7, line 10, the printed patent incorrectly reads "active species $R^{III}$". The patent should read --active species $Ru^{III}$--.

At column 9, line 26, the printed patent incorrectly reads "generate the highly active species $R^{III}$-P". The patent should read --generate the highly active species $Ru^{III}$-P--

At column 9, line 62, the printed patent incorrectly reads "with a suitable anion such as $SbF_6^{31}$ or". The patent should read --with a suitable anion such as $SbF_6^-$ or--.

At column 14, line 11, the printed patent incorrectly reads "1-octene to the $R^{III}$". The patent should read --1-octene to the $Ru^{III}$--.

At column 14, line 16, the printed patent incorrectly reads "oxidation of $R^{III}$". The patent should read --oxidation of $Ru^{III}$--.

At column 14, line 36, the printed patent incorrectly reads "catalytic species complex 3 ($Re^{III}$)". The patent should read --catalytic species complex 3 ($Ru^{III}$)--.

At column 14, lines 50, the printed patent incorrectly reads "$R^{III}$". The patent should read --$Ru^{III}$--.

UNITED STATES PATENT AND TRADEMARK OFFICE
CERTIFICATE OF CORRECTION

PATENT NO. : 6,002,026
DATED : December 14, 1999
INVENTOR(S) : Groves et al.

It is certified that error appears in the above-indentified patent and that said Letters Patent is hereby corrected as shown below:

At column 15, line 53, the printed patent incorrectly reads "In the absence of catalyst the ,β". The patent should read --In the absence of catalyst the α, β --.

At column 17, line 49, the printed patent incorrectly reads "goes to $R^{III}$". The patent should read --goes to $Ru^{III}$--.

Signed and Sealed this

Sixteenth Day of January, 2001

Attest:

Q. TODD DICKINSON

*Attesting Officer*  *Commissioner of Patents and Trademarks*